(12) United States Patent
Lundahl et al.

(10) Patent No.: US 11,724,008 B2
(45) Date of Patent: Aug. 15, 2023

(54) HYDROPHILIC MEDICAL DEVICE

(71) Applicant: DENTSPLY IH AB, Mölndal (SE)

(72) Inventors: Johan Lundahl, Gothenburg (SE); Åsa Rindlav Westling, Lindome (SE)

(73) Assignee: DENTSPLY IH AB, Mölndal (SE)

( * ) Notice: Subject to any disclaimer, the term of this patent is extended or adjusted under 35 U.S.C. 154(b) by 1172 days.

(21) Appl. No.: 16/336,061

(22) PCT Filed: Dec. 22, 2016

(86) PCT No.: PCT/EP2016/082410
§ 371 (c)(1),
(2) Date: Mar. 22, 2019

(87) PCT Pub. No.: WO2017/114753
PCT Pub. Date: Jul. 6, 2017

(65) Prior Publication Data
US 2019/0224384 A1      Jul. 25, 2019

(30) Foreign Application Priority Data
Dec. 28, 2015   (EP) ..................... 15202776

(51) Int. Cl.
*A61L 29/08*      (2006.01)
*A61L 29/14*      (2006.01)
(Continued)

(52) U.S. Cl.
CPC ............. *A61L 29/085* (2013.01); *A61L 29/02* (2013.01); *A61L 29/14* (2013.01);
(Continued)

(58) Field of Classification Search
CPC ............. A61L 2400/10; A61L 2420/02; A61L 2420/06; A61L 28/085; A61L 29/02;
(Continued)

(56) References Cited

U.S. PATENT DOCUMENTS 4,642,267 A * 2/1987 Creasy .................... C08L 39/06
428/413
4,781,978 A * 11/1988 Duan ................... C09D 133/24
428/383
(Continued)

FOREIGN PATENT DOCUMENTS

JP      2009501608 A      1/2009
JP      2009515604 A      4/2009
(Continued)

OTHER PUBLICATIONS

"Poly(vinylpyrrolidone), PVP". Accessed at https://polymerdatabase.com/polymers/polyvinylpyrrolidone.html, 2015.*
(Continued)

*Primary Examiner* — Bhisma Mehta
*Assistant Examiner* — John J Crawford
(74) *Attorney, Agent, or Firm* — Perkins Coie LLP

(57) ABSTRACT

A medical device, such as a catheter, is disclosed, comprising a substrate and having on its surface, on at least a part thereof, a hydrophilic surface layer providing low-friction surface character of the medical device when wetted by a wetting fluid. At least one base layer of the substrate, including the hydrophilic surface layer, is made of a polymer blend comprising at least one base polymer and at least one hydrophilic polymer, and wherein the concentration of the at least one hydrophilic polymer is higher in the hydrophilic surface layer than in the rest of the base layer. A method for producing such a medical device is also disclosed.

19 Claims, 2 Drawing Sheets

(51) Int. Cl.
*B05D 5/08* (2006.01)
*A61L 29/02* (2006.01)

(52) U.S. Cl.
CPC ....... *A61L 2400/10* (2013.01); *A61L 2420/02* (2013.01); *A61L 2420/06* (2013.01); *B05D 5/08* (2013.01)

(58) Field of Classification Search
CPC ........... A61L 29/14; A61M 2205/0222; A61M 2025/0062
See application file for complete search history.

(56) References Cited

U.S. PATENT DOCUMENTS

| | | | | |
|---|---|---|---|---|
| 5,041,100 A | * | 8/1991 | Rowland | A61M 25/0045 604/265 |
| 5,061,424 A | * | 10/1991 | Karimi | A61L 29/049 264/173.19 |
| 5,443,907 A | * | 8/1995 | Slaikeu | A61M 25/09 428/375 |
| 5,688,855 A | * | 11/1997 | Stoy | A61L 29/085 524/113 |
| 6,848,574 B1 | | 2/2005 | Israelsson et al. | |
| 2004/0133156 A1 | * | 7/2004 | Diaz | A61M 25/1027 604/96.01 |
| 2007/0184275 A1 | | 8/2007 | Gilman | |
| 2009/0155519 A1 | * | 6/2009 | Lee | A61L 31/10 428/67 |
| 2009/0200187 A1 | | 8/2009 | Nestenborg et al. | |
| 2010/0159116 A1 | | 6/2010 | Rindlaw-Westling et al. | |
| 2011/0071507 A1 | * | 3/2011 | Svensson | A61M 25/001 604/544 |
| 2012/0077049 A1 | * | 3/2012 | Lin | A61L 31/14 428/520 |
| 2014/0193474 A1 | * | 7/2014 | Babcock | C10M 107/28 424/422 |
| 2018/0126035 A1 | * | 5/2018 | O'Mahony | A61L 29/085 |

FOREIGN PATENT DOCUMENTS

| | | |
|---|---|---|
| JP | 2009525176 A | 7/2009 |
| WO | 2007011287 A1 | 1/2007 |
| WO | 2007081603 A2 | 7/2007 |
| WO | 2007089784 A2 | 8/2007 |

OTHER PUBLICATIONS

Office Action dated Sep. 23, 2020 for Japanese Patent Application No. 2018-533063 (4 pages).
Extended European Search Report for European Patent Application No. 15202776.9, dated Jun. 8, 2016 (8 pages).
International Search Report and Written Opinion for International Patent Application No. PCT/EP2016/082410, dated Mar. 7, 2017 (11 pages).

* cited by examiner

US 11,724,008 B2

HYDROPHILIC MEDICAL DEVICE

CROSS REFERENCE TO RELATED APPLICATIONS

This patent document is a 371 National Phase Application of International Patent Application No. PCT/EP2016/082410, filed Dec. 22, 2016, which claims priority to European Patent Application No. 15202776.9, filed Dec. 28, 2015. The entire contents of the aforementioned patent applications are incorporated by reference as part of the disclosure of this patent document.

FIELD OF THE INVENTION

The present invention generally relates to a hydrophilic medical device, and in particular a medical device which present a substrate, such as an elongate shaft, having a hydrophilic surface which exhibits low-friction when wetted. In particular the invention relates to a catheter for insertion into a passageway in a human or animal body, and specifically urinary catheters. The invention is also related to a corresponding method of manufacture.

BACKGROUND OF THE INVENTION

Many medical devices incorporate elongate shafts such as tubes which are intended for insertion into and through passageways of a living body such as those of the urethral tract and the cardiovascular system. The most common type of this general grouping of medical devices is known as catheters. Exemplary catheters include those designated for urological, angioplasty and valvuloplasty uses, that is, adapted respectively for insertion into the urethra, the lumen of a blood vessel and heart passageway of a living body, normally a human body.

Because of the intended use of such medical devices, such as use as a urinary catheter, certain parameters need to be satisfied by the material from which the elongate shaft is manufactured. The material must fulfill such requirements as softness, good kink resistance, good dimensional stability, processability, for example ease to form and glue, and the possibility to be sterilized by radiation, steam, gas (e.g. ethylene oxide) or other means. For many products, there is further the need for the material to have a low-friction surface. This may be obtained by arranging a hydrophilic coating on the substrate of the medical device.

However, provision of an adequate hydrophilic coating may be problematic. For example, the chemistry of the substrate material is critical since this affects the possibility to coat the substrate. Further, the coating process is often cumbersome and costly. The coating process also typically involves solvents and the like, thereby making the coating processes environmentally unsatisfying. Still further, the resulting hydrophilic coating may be inadequate, and e.g. being insufficiently connected to the substrate, etc.

Thus, there is a general problem for most previously known hydrophilic medical devices, that they are costly and/or harmful to the environment, and/or that there are problems related to the hydrophilic coating, such as too poor water retention properties, especially after leaching, too poor adherence to the substrate and too high friction of the hydrophilic surface when wetted. Further, alternatively or additionally, the mechanical properties of the substrates may be inadequate, such as being too stiff or having too high resilience. Further, the coating quality may be affected and deteriorated during storage, and many medical devices, such as urinary catheters, should typically have a shelf life of at least 2 years, and preferably 3 years or 3.5 years, and many known hydrophilic coatings have problem in maintaining adequate quality during such long time storage.

There is therefore still a need for a new hydrophilic medical device, i.e. a medical device having a hydrophilic surface, which at least partly alleviates the above-discussed problems.

SUMMARY OF THE INVENTION

It is a general object of the present invention to alleviate the above-discussed problems.

This object is fulfilled by a medical device and a method in accordance with the appended claims.

According to a first aspect of the present invention, there is provided a medical device comprising a substrate, having on its surface, on at least a part thereof, a hydrophilic surface layer providing low-friction surface character of the medical device when wetted by a wetting fluid, wherein at least one base layer of the substrate, said base layer including said hydrophilic surface layer, is made of a polymer blend comprising at least one base polymer and at least one hydrophilic polymer, and wherein the concentration of said at least one hydrophilic polymer is higher in the hydrophilic surface layer than in the rest of the base layer.

In this medical device, the hydrophilic surface layer is formed as an integral part of the substrate, e.g. by means of the method disclosed in the following. Thus, even though there is no hydrophilic coating, the medical device is provided with a hydrophilic surface layer serving the same purpose, and having similar properties, as a conventional hydrophilic surface coating. In addition, the hydrophilic surface layer of this invention can be formed quicker, easier and more cost-efficiently than previously known hydrophilic coatings, and in particular, the production lends itself excellently for fully automated manufacturing. Still further, the hydrophilic surface layer is very robust and stable, being e.g. strongly connected to the rest of the substrate.

The substrate may be formed in its entirety by the base layer, and thus be entirely formed by the specified polymer blend. However, the substrate may also comprise one or more additional support layer(s), preferably being arranged inside or underneath the base layer. For example, the base layer may be attached to a support layer (or second base layer) made of a thermoplastic polymer material, such as polyurethane, polyolefin or the like. In case of a catheter, such an additional support layer is preferably arranged inside the base layer comprising the specified polymer blend, so that the hydrophilic surface layer faces the exterior of the catheter. Attachment of the base layer to a further support layer may be obtained in various ways, such as by co-extrusion and the like.

In experiments it has been concluded that this hydrophilic surface layer provides excellent water retention, excellent stability of the surface layer and adherence to the substrate, and excellent low-friction properties of the surface when wetted with a wetting fluid, both immediately after wetting and for an extended period of time.

The concentration of the hydrophilic polymer may be essentially the same in the entire of the interior of the base layer.

Further, there may be a thin transition layer between the hydrophilic surface and the interior of the base layer, the transition layer providing a gradual increase in concentration of the hydrophilic polymer from the interior of the base layer towards the hydrophilic surface. However, depending on the manufacturing process, the transition layer can be made extremely thin, and in some cases close to non-detectable.

The hydrophilic surface layer preferably comprises a very high concentration of the hydrophilic polymer(s). In particular, the material composition of the hydrophilic surface layer preferably comprises at least 70 wt % of the at least one polymer, and preferably at least 80 wt %, and more preferably at least 90 wt %, and even more preferably at least 95 wt %, and most preferably at least 99 wt %. These and other concentrations related to the material composition of the substrate and the surface layer are all directed to a dry, non-wetted state, i.e. excluding the content of wetting fluid used for wetting the hydrophilic surface layer for the intended use.

The interior of the base layer also comprises a significant concentration of the hydrophilic polymer(s), but in a lower concentration than in the hydrophilic surface layer. The polymer blend in the interior of the base layer preferably comprises 20-90 wt % of the at least one hydrophilic polymer, and preferably 25-75 wt %, and most preferably 25-50 wt %.

The polymer blend also comprises a significant concentration of the base polymer(s). The polymer blend in the interior of the base layer preferably comprises 20-80 wt % of the at least one base polymer, and preferably 25-75 wt %, and most preferably 50-75 wt %.

The cross-linked hydrophilic surface layer is preferably relatively thin, and e.g. being only a few micrometers thick when dry. The hydrophilic surface layer is preferably a single layer of hydrophilic polymer that extends into the interior of the base layer of the substrate. The interior of the base layer may itself have a gradient of increasing hydrophilic polymer towards its surface, making the transition gradual between hydrophilic surface layer and the interior of the base layer. Preferably, the interior of the base layer forms at least 95% of the total thickness of the base layer (or the total thickness of the substrate, in case there are no additional support layers), and preferably at least 99% and most preferably at least 99.9%. Correspondingly, the hydrophilic surface layer preferably has a thickness which is less than 1% of the total thickness of the base layer (or of the total thickness of the substrate, in case there are no additional support layers), and preferably less than 0.1%. These thickness measures relate to a dry state, i.e. where the hydrophilic surface layer is not wetted (even though it may previously have been wetted during production, as will be discussed in more detail below). Alternatively or additionally, it is preferred that the hydrophilic polymer layer has a thickness of less than 10% of the total thickness of the base layer in a wetted state, and preferably less than 1%, and more preferably less than 0.1%. The gradient zone, i.e. the transition layer, in the base layer may e.g. be from 1% of the total thickness of the base layer and up to the entire interior of the base layer.

When reference is made to a "dry state" this refers to a state where the materials are as dry as they get under normal conditions in indoor atmosphere. For many materials, such a dry state is completely dry, but some hygroscopic materials contain a small amount of water also in a normal state, and this natural state is also regarded as a dry state in the context of the present application. However, also in such hygroscopic materials, the water content is very limited in a normal state. Thus, the water content in any material in the dry state is preferably below 5 wt %, and more preferably below 2 wt %, and most preferably below 1 wt %.

The at least one hydrophilic polymer may comprise at least one material selected from: polyvinyl compounds, polysaccharides, polyurethanes, polyacrylates or copolymers of vinyl compounds and acrylates or anhydrides, poly (alkyl ether), i.e. polyethylene oxide or polypropylene oxide, such as polyoxyethylene (POE), and in particular polyethylene oxide (PEO), polyvinyl-pyrrolidone, heparin, dextran, xanthan gum, polyvinyl alcohol, hydroxy propyl cellulose, methyl cellulose, copolymer of vinylpyrrolidone and hydroxy ethylmethyl acrylate or copolymer of polymethylvinyl ether and maleinic acid anyhydride, and copolymers of these. The term polyoxyethylene is here used to include polymer chains of any molecular weight, thereby including both polyethylene glycol (PEG), having a molecular weight below 20,000 g/mol, and polyethylene oxide (PEO), having a molecular weight above 20,000 g/mol.

Preferably, the hydrophilic polymer is a meltable polymer.

The hydrophilic polymer is preferably at least one of polyethylene oxide, poly(acrylic acid), polyvinyl-pyrrolidone and polysaccharide, such as carboxy methyl cellulose. In a particularly preferred embodiment, the hydrophilic polymer(s) comprises polyethylene oxide.

The hydrophilic polymer(s) preferably has a relatively high molecular weight. Preferably, the hydrophilic polymer(s) has a molecular weight of at least 50 kDa, and preferably at least 100 kDa, and most preferably at least 200 kDa.

The at least one base polymer is preferably a predominantly hydrophobic polymer.

In one embodiment, the at least one base polymer comprises at least one of polyolefin and polyurethane, such as thermoplastic polyurethane. Preferably, the at least one base polymer comprises at least 20 wt % of polyolefin and/or polyurethane, and preferably at least 25 wt %, and more preferably at least 50 wt %, and more preferably at least 75 wt %, and most preferably at least 90 wt %.

In case polyolefin is used, the polyolefin may comprise at least one polymer selected from the group: polyethylene, polypropylene, and olefinic thermoplastic elastomers i.e. styrene block copolymer (SEBS). The base polymer(s) may also comprise polyolefin and at least one composition having molecules with active hydrogen(s), the molecules preferably being molecules where the active hydrogen(s) is bound to the molecules via nitrogen. The compound having molecules with active hydrogen(s) can be either a polymer or smaller molecules, or various combinations of such polymers/molecules. Molecules with active hydrogen(s) are molecules having hydrogen that is proned to react with other substances, and thus to leave its position in the molecule. Examples of such compositions having molecules with active hydrogen groups are alcohols, amides, amines, urethanes and acids, and in particular amides, amines and urethanes are preferred.

The polyolefin is a material comprising olefin monomers, such as one or several of ethylene, propylene, butadiene, pentene, etc. The polyolefin can comprise intermixed medical oil, i.e. oil of medical grade, and/or paraffin. Polyolefins can be made cost effective and with good mechanical properties for use e.g. as a catheter, and in particular for urinary catheters, and with good environmental properties. However, with polyolefin substrates it is relatively difficult to obtain a good adherence for a hydrophilic surface coating. However, it has been found that the polyolefin based substrates can relatively easy be provided with hydrophilic surface layers, in the way discussed in more detail in the following, thereby providing a very robust and stable hydrophilic surface layer with excellent properties. Further, the excellent mechanical properties of the polyolefin can be maintained, making the substrate highly useable for many types of medical devices, such as for urinary catheters.

The base layer may further comprise a filler material, such as calcium carbonate filler. For example, the substrate may comprise 1-20 wt % of filler material, and preferably 2-10 wt %. Preferably, the filler material is a low price material which does not significantly alter the properties of the substrate, or its useability as the intended medical device, but makes the overall costs for the medical device lower.

Instead of being entirely homogeneous, the interior of the base layer may comprise at least two different sub-layers, wherein an outer sub-layer, being closer to the hydrophilic surface layer, has a higher concentration of the hydrophilic polymer(s) than an inner sub-layer, being farther from said hydrophilic surface layer. These two different sub-layers may e.g. be coextruded together. Such arrangement of two or more different sub-layers may e.g. be used to obtain the desired mechanical properties of the medical device, to lower the overall material costs, etc.

As discussed in the foregoing, the base layer may also be arranged on one or more additional support layers, e.g. by co-extrusion. This may also be used to obtain the desired mechanical properties of the medical device, to lower the overall material costs, etc.

The medical device is preferably a catheter, and preferably a urinary catheter, wherein the hydrophilic surface layer is provided at least on an insertable part thereof. Most preferably, the medical device is a urinary catheter for intermittent catheterization, i.e. for intermittent, short time use. The urinary catheter preferably has an internal lumen extending between an outlet opening, preferably arranged in the form of a flared connector, and drainage openings arranged close to the proximal, insertable end of the catheter. The insertable tip of the catheter is preferably closed, and is preferably formed in a rounded shape. Preferably, only one, single lumen is provided in the catheter.

In order to obtain good mechanical properties, the substrate preferably has a hardness Shore A in the range 75-85, and preferably within the range 78-82.

It is further preferred that the substrate has a radiation resistance such that it can endure at least 25 kGy, and preferably at least 50 kGy, essentially without degradation. Hereby, radiation sterilization of the medical device can be used, without affecting the properties of the medical device.

The forming of the base layer and the substrate from said polymer blend is preferably made by means of extrusion, co-extrusion or molding, such as injection molding, or other melt forming processes.

According to another aspect, there is provided a corresponding method for production of a medical device discussed in the foregoing. Thus, there is provided a method for producing a medical device, and preferably a catheter, such as a urinary catheter, comprising:

preparing a polymer blend comprising at least one base polymer and at least one hydrophilic polymer;

forming a substrate including at least one layer made from said polymer blend;

arranging the substrate in a wetting liquid, whereby the at least one hydrophilic polymer migrate(s) towards a surface of the substrate; and irradiating the substrate, thereby forming cross-linking between the polymers, thereby prohibiting further migration of the hydrophilic polymer(s), whereby a stable hydrophilic surface layer, comprising a higher concentration of the hydrophilic polymer(s) than said polymer blend, is formed on the surface of the substrate.

This method is particularly useful to provide the novel and advantageous type of medical devices discussed above. The production method is further relatively simple and quick, and can be used for very cost-effective manufacturing. The method is also easy to integrate in fully or partly automated manufacturing.

The radiation is preferably at least one of gamma radiation, beta radiation, E-beam and UV radiation. Preferably, the radiation is ionizing radiation, and most preferably E-beam or gamma radiation. The absorbed dose in the irradiated medical device is preferably at least 25 kGy, such as at least 50 kGy.

The step of arranging the substrate in a wetting liquid preferably comprises arranging the medical device in a container together with the wetting liquid, and closing the container, and wherein the subsequent irradiating step also effects sterilization of the medical device. Since medical devices of this type often need to be sterilized, and since it in some cases may be wanted to have medical devices of this type to be constantly maintained in a wetting fluid, in an activated ready-to-use state, this means that even fewer steps are needed, providing a much more efficient and less costly manufacturing process compared to conventional manufacturing, but at the same time providing a low friction hydrophilic surface layer with excellent properties, and without the need for any coating process.

It has been found that the waiting time between the arrangement of the medical device in the wetting liquid and the irradiation may be controlled in order control the properties of the hydrophilic surface layer. Hereby, it becomes possible to control e.g. the thickness of the hydrophilic surface layer, the concentration of the hydrophilic polymer (s) in the surface layer, etc, in a very simple but yet very efficient way. The waiting time may be controlled to be in the range 1 minute to 24 hours, and preferably in the range 2 minutes to 4 hours, and most preferably in the range 3-180 minutes.

No pretreatment of the substrate prior to the wetting is generally needed or desired. However, optionally e.g. the degree and speed of migration and/or cross-linking may be controller also by additional pretreatment, such as irradiation with UV prior to wetting, plasma treatment and the like. Such pretreatment could also, optionally be used to obtain varying properties at different areas of the substrate. For example, it may be used to lower friction at certain parts, e.g. in the insertion tip area, to provide higher friction at certain parts, e.g. at or in the vicinity of the non-insertable end, etc.

By "fluid" is in the context of the present application meant the conventional meaning of the term, including any media that flows under shear stress, and in particular including both liquids and gases. The wetting fluid may e.g. be vapor or steam, or a wetting liquid, which may be water or an aqueous solution, such as isotonic or hypertonic solution, such as isotonic or hypertonic saline solution.

According to still another aspect of the present invention, there is provided a medical device assembly, comprising a medical device as discussed in the foregoing, and a container and a wetting fluid, wherein said container houses at least a part, and preferably the entire, medical device together with the wetting fluid, so that at least a part, and preferably the entire, hydrophilic surface layer is maintained in a wetted state. For example, the whole or part of the medical device may be maintained in direct contact with the wetting fluid, or be pre-wetted, so that the wetting fluid is present essentially only in the medical device and not in the rest of the container.

Hereby, similar properties and advantages as discussed above in relation to the other aspects of the invention are obtainable.

These and other aspects of the inventive concept will be apparent from and elicited with reference to the embodiments described hereinafter.

BRIEF DESCRIPTION OF THE DRAWINGS

By way of example embodiments of the invention will now be described with reference to the accompanying drawings in which.

DESCRIPTION OF PREFERRED EMBODIMENTS

Figure 1:
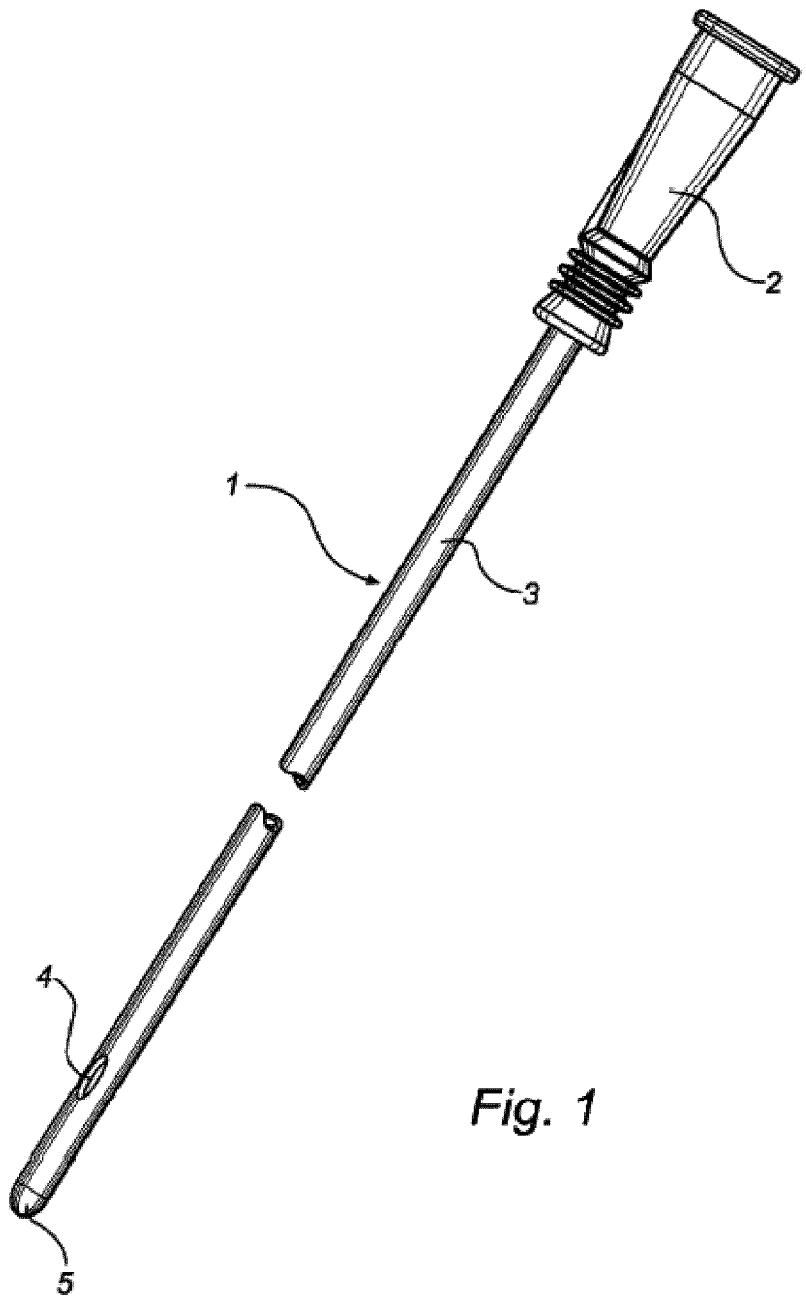
FIG. 1 illustrates an embodiment of a catheter according to the invention.

In the following detailed description preferred embodiments of the invention will be described. However, it is to be understood that features of the different embodiments are exchangeable between the embodiments and may be combined in different ways, unless anything else is specifically indicated. It may also be noted that, for the sake of clarity, the dimensions of certain components illustrated in the drawings may differ from the corresponding dimensions in real-life implementations of the invention, e.g. the length of the catheter. Further, even though the following detailed description focuses on a urinary catheter, it is to be appreciated by the skilled reader but is equally applicable to other types of catheters, e.g. intended to be introduced into other type of body-cavities than the urethra, and is also applicable to many other types of medical devices having a need for a hydrophilic surface.

A catheter 1 as illustrated in FIG. 1, comprises a flared rearward portion 2 and an elongate shaft or tube 3 projecting forwardly from the rearward portion 2. An open-ended internal lumen (not shown) extends from the rear end of the rearward portion 2 to a drainage aperture 4 in a rounded tip 5 of the elongate tube 3. The catheter preferably has only one, single internal lumen. The drainage openings are preferably arranged close to the proximal, insertable end of the catheter. The insertable tip of the catheter is preferably closed, and is preferably formed in a rounded shape. The rearward portion 2 is preferably formed as a flared end, and may function as a connector of the catheter 1, being connectable to other devices, such as a urine collection bag, a drainage tube or the like.

At least a part of the elongate tube 3 forms an insertable length to be inserted through a body opening of the user, such as the urethra in case of a urinary catheter. By insertable length is normally meant that length of the elongate tube 2 which is insertable into the urethra of the patient. Typically, this will be 80-140 mm for a female patient and 200-350 mm for a male patient. At least the insertable part of the catheter is preferably provided with a hydrophilic surface layer, to be discussed in more detail in the following.

The catheter is preferably arranged in a closed container, functioning as a package, and optionally also as a sterile barrier, in a sterilized state. The container houses at least the insertable part of the catheter, and preferably also a wetting fluid to maintain the catheter in an activated, wetted state. Hereby, the catheter becomes immediately ready to use upon withdrawal from the package.

Figure 2:
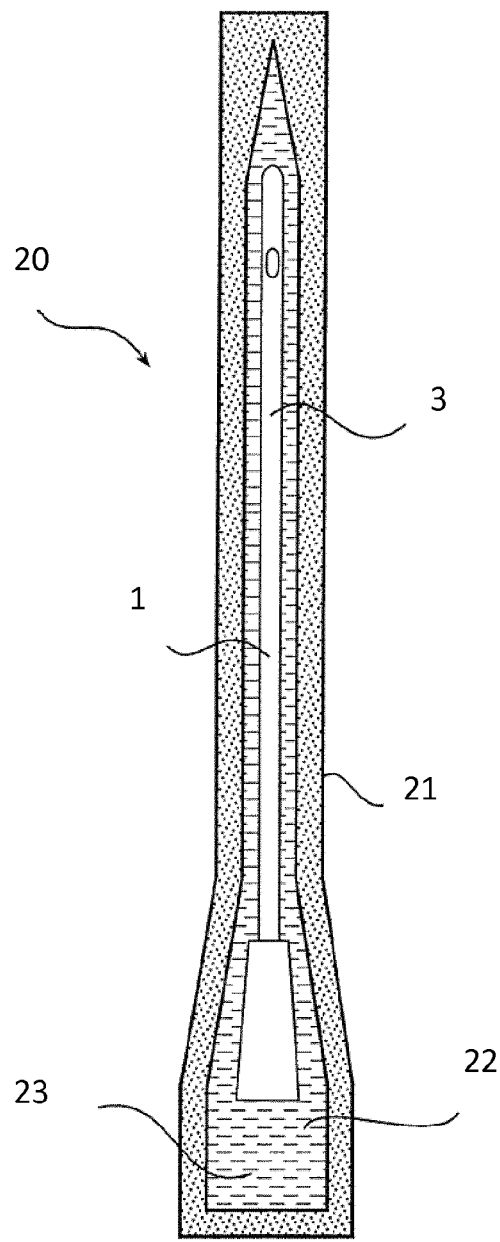
FIG. 2 is a cross-sectional view of an exemplary catheter assembly in accordance with an embodiment of the invention.

In FIG. 2, a catheter assembly 20 is schematically illustrated in which the entire catheter 1 is enclosed within the container 21. Here, it is preferred that the entire catheter is arranged in contact with the wetting fluid 23, thereby ensuring that an adequate wetting is maintained at all times. The container is preferably made of a gas-impermeable material, such as a material comprising an aluminum barrier layer. The container is preferably arranged with a shape resembling the shape of the catheter, having a narrow elongate part housing the insertable part of the catheter, and a somewhat wider rearward part 22, housing the connector end of the catheter. Hereby, the package encloses the catheter narrowly, thereby limiting the volume between the catheter and the package walls. This type of package is per se further disclosed in U.S. Pat. No. 6,848,574 by the same applicant, said patent hereby being incorporated in its entirety by reference. However, the container may also have many other shapes and dimensions, such as being rectangular etc.

Figure 3:
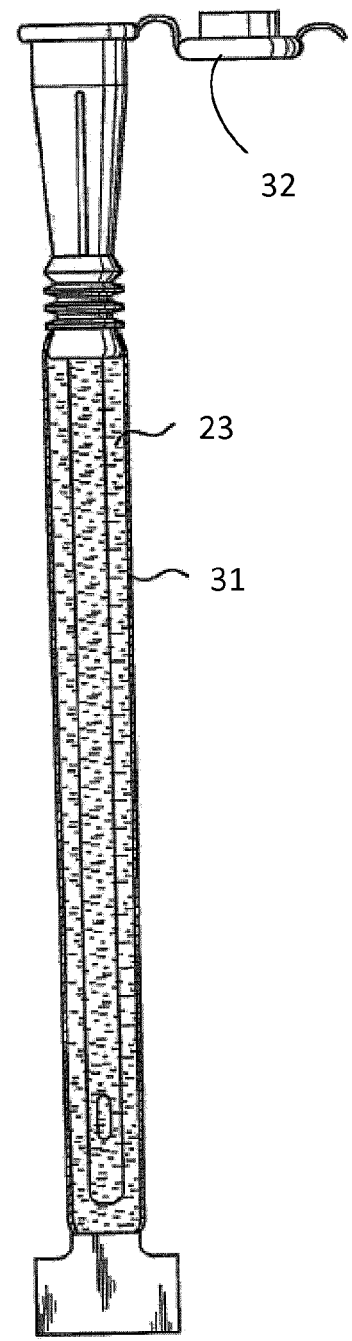
FIG. 3 is a cross-sectional view of an exemplary catheter assembly in accordance with another embodiment of the invention.

In FIG. 3, an alternative embodiment of a catheter assembly is illustrated. Here, only a part of the catheter, including the insertable part, is enclosed within the package together with the wetting fluid.

The receptacle 31 could e.g. be connected to the catheter, and in particular to the connector. For example, the connection could be provided by means of a welding joint arranged between the catheter and the receptacle, or by means of a shrink fit, an adhesive or the like. The catheter lumen may be closable by means of a cap or cover 32 arranged to sealingly close the connector opening. However, other ways of providing a closure of the lumen are feasible as well, such as arranging a breakable membrane somewhere in the lumen.

The wetting fluid 23 is here in contact only with the catheter shaft. Thus, the entire insertable, hydrophilic part is maintained immersed in the wetting fluid, whereas non-insertable parts are to at least some extent outside the package, and without contact with the wetting fluid. However, similar to the embodiment above, the catheter is maintained in a activated, ready-to-use condition. In order to preserve this wetted condition the compartment formed by the receptacle and the catheter is preferably gas sealed, and further, the receptacle is preferably gas impermeable. Catheter assemblies of this general type are further disclosed in US 2009/0200187 by the same applicant, said document hereby being incorporated in its entirety by reference.

In use, the receptacle may, in both the embodiments discussed above, simply be opened, and the catheter could immediately be introduced into the patient.

The receptacle housing the wetting fluid and part of or the whole catheter is preferably a gas impermeable material. For example one or several of the following gas impermeable materials could be used: aluminium foil laminate, poly (vinylidene chloride) or laminate comprising a metallised film, such as metallised poly(ethylene terepthalate), or silicon oxide coated film, or a laminate comprising aluminum oxide.

In case the catheter is maintained in a wetted state during storage, such as in the above-discussed assembly embodiments, the catheter is immediately ready for use and insertion upon withdrawal from the container. In this ready-so-use case, the catheter may be stored immersed in a wetting liquid, as discussed in the foregoing. However, the catheter may also be stored in an activated state, where all wetting fluid is present within the hydrophilic surface layer and no or very limited excess wetting fluid is present in the rest of the container. Further, the wetting fluid need not be present in liquid form, but may also be present in the form of gas, e.g. by providing a moist, vapor containing atmosphere in the container. However, the catheter may also be stored in a dry state. In such a case, the wetting fluid may be arranged in a separate compartment or pouch of the package, for wetting and activation of the catheter immediately prior to use. When maintained in a dry state, it is also possible to wet the catheter with a wetting fluid provided from an external supply.

The wetting fluid is preferably a water-based liquid, i.e. using plain water or a solution comprising water as a solvent, such as saline or other.

The catheter tubing substrate material is produced by preparing a polymer blend comprising at least one base polymer and at least one hydrophilic polymer and forming a substrate or a base layer in the substrate from said polymer blend. The preparation of the blend may be made by a compounding step. The forming may e.g. be obtained by extrusion. The substrate is then arranged in a wetting liquid. Hereby, the at least one hydrophilic polymer migrate(s) towards a surface of the substrate. After a sufficient waiting time, which may amount to only a few minutes, or which may have a duration of hours or even days, the substrate is irradiated, thereby forming cross-linking between the polymers. This cross-linking prohibits further migration of the hydrophilic polymer(s), whereby a stable hydrophilic surface layer, comprising a higher concentration of the hydrophilic polymer(s) than said polymer blend, is formed on the surface of the substrate.

Thus, the resulting catheter comprises on at least a part thereof, a hydrophilic surface layer providing low-friction surface character of the medical device when in wet state, and the substrate, or at least a base layer of the substrate, is made of a polymer blend comprising the at least one base polymer and the at least one hydrophilic polymer, and wherein the concentration of said at least one hydrophilic polymer is higher in the hydrophilic surface layer than in the interior of the base layer or substrate. Thus, the hydrophilic surface layer is formed not as a coating, but as an integral part of the base layer or substrate.

The substrate may be formed in its entirety by the base layer, and thus be entirely formed by the specified polymer blend. However, the substrate may also comprise one or more additional support layer(s), preferably being arranged inside or underneath the base layer. For example, the base layer may be attached to a support layer (or second base layer) made of a thermoplastic polymer material, such as polyurethane, polyolefin or the like. In case of a catheter, such an additional support layer is preferably arranged inside the base layer comprising the specified polymer blend, so that the hydrophilic surface layer faces the exterior of the catheter. Attachment of the base layer to a further support layer may be obtained in various ways, such as by co-extrusion and the like.

The step of arranging the substrate in a wetting liquid preferably comprises arranging the medical device in the container together with the wetting liquid, and closing the container, as illustrated in FIGS. 2 and 3. Hereby, the subsequent irradiating step may also effect sterilization of the medical device.

The concentration of the hydrophilic polymer may be essentially the same in the entire of the interior of the base layer or substrate, i.e. with a homogeneous blend throughout the interior of the base layer/substrate. However, instead of being entirely homogeneous, the interior of the base layer may comprise at least two different sub-layers, wherein an outer sub-layer, being closer to the hydrophilic surface layer, has a blend of base polymer(s) and hydrophilic polymer(s) with a higher concentration of the hydrophilic polymer(s) than in the corresponding blend of the inner sub-layer, being farther from said hydrophilic surface layer. These two different sub-layers, which both comprise blends of base polymer(s) and hydrophilic polymer(s), may e.g. be coextruded together.

The at least one hydrophilic polymer may comprise at least one material selected from: polyvinyl compounds, polysaccharides, polyurethanes, polyacrylates or copolymers of vinyl compounds and acrylates or anhydrides, poly (alkyl ether), i.e. polyethylene oxide or polypropylene oxide, such as polyoxyethylene (POE), and in particular polyethylene oxide (PEO), polyvinyl-pyrrolidone (PVP), heparin, dextran, xanthan gum, polyvinyl alcohol, hydroxy propyl cellulose, methyl cellulose, copolymer of vinylpyrrolidone and hydroxy ethylmethyl acrylate or copolymer of polymethylvinyl ether and maleinic acid anyhydride, and copolymers of these. Preferably, the hydrophilic polymer is a meltable polymer.

The hydrophilic polymer is preferably at least one of polyethyleneoxide (PEO), poly(acrylic acid), polyvinyl-pyrrolidone (PVP) and polysaccharide, such as carboxy methyl cellulose. In a particularly preferred embodiment, the hydrophilic polymer(s) comprises polyethyleneoxide.

The hydrophilic polymer(s) preferably has a relatively high molecular weight. Preferably, the hydrophilic polymer(s) has a molecular weight of at least 50 kDa, and preferably at least 100 kDa, and most preferably at least 200 kDa.

The at least one base polymer is preferably a predominantly hydrophobic polymer. For example, the at least one base polymer may comprise at least one of polyolefin and polyurethane, such as thermoplastic polyurethane.

In case polyolefin is used, the polyolefin may comprise at least one polymer selected from the group: polyethylene, polypropylene, and styrene block copolymer (SEBS). The base polymer(s) may also comprise polyolefin and at least one composition having molecules with active hydrogen(s), the molecules preferably being molecules where the active hydrogen(s) is bound to the molecules via nitrogen. The compound having molecules with active hydrogen(s) can be either a polymer or smaller molecules, or various combinations of such polymers/molecules. Examples of such compositions having molecules with active hydrogen groups are alcohols, amides, amines, urethanes and acids, and in particular amides, amines and urethanes are preferred.

The base layer or substrate may further comprise a filler material, such as calcium carbonate filler.

In order to obtain good mechanical properties, the substrate materials is preferably prepared and composed in such a way that it fulfills at least some of the following requirements, and preferably essentially all of them:

The material should have a hardness adequate for the intended use. For example for urinary catheter, the hardness Shore A should preferably be in the range 75-85, and most preferably within the range 78-82.

Possibility to be sterilized by known sterilization methods. In particular it is preferred that the substrate has a radiation resistance such that it can endure at least 25 kGy, and preferably at least 50 kGy, essentially without degradation, in order to enable radiation sterilization of the medical device.

The material should exhibit low resilience.

The material should have good kinking properties.

The material should preferably be meltprocessable, extrudable, or usable for molding, and in particular useable for injection molding.

The substrate material should preferably be biocompatible.

The substrate material should preferably have good dimension stability. In particular, it is preferred that the longitudinal shrinkage of the catheters as a result of the coating process is less than 5%, and preferably less than 1%, of the original length.

Experiments

In a first line of comparative experiments, a PEO coating was co-extruded on top of a poyolefin based substrate. However, it was found that the resulting coated substrates were not useable for catheters. The PEO coating became very thick, uneven and eventually dissolved when wetted.

In a second line of comparative experiments, attempts were made to make the substrate solely of PEO. Even though this substrate has adequate low friction properties on the surface, it could not be used as a catheter material. During wetting, the substrate was severely deformed, swelled extensively, became unstable, with poor mechanical properties, etc.

In experiments in accordance with the invention, the following materials were used:

PEO: Polyox WSR N80 from Dow Chemical. This polyethyleneoxide is meltable, and has a molecular weight of about 200 kDa.

PVP: PVP K90, sold by e.g. Sigma Aldrich. This polymer disintegrates at about 190 deg. C. but blends well below such temperatures, and has a molecular weight of above 300 kDa.

T60: A thermoplastic polyurethane, sold as Tecophil HP-60D-20 by Lubrizol, having components allowing some uptake of water.

T93: A thermoplastic polyurethane, sold as Tecophil HP-93-A-100 by Lubrizol, having components allowing even higher uptake of water (i.e. higher than for T60).

PU: A thermoplastic polyurethane with very low hydrophilicity, sold as Pellethane 5863-82AE by Lubrizol.

PB: A polyolefin base polymer based on the commercially available polyolefin material Meliflex®.

PE: A block copolymer of polybutylene terephthalate (PBT) and polyether glycol terephthalate sold under the tradname Skypel by SK Chemicals.

Filler: A calcium carbonate filler, Imercarb 10L, from Imerys Carbonates.

Compatibilizer: Fusabond E226 from DuPond.

In a first line of experiments, various blends where prepared, comprising different blends of a base polymer and PEO. The blends were compounded by means of a Brabender compounder. The hygroscopic materials, such as T60, T93 and PEO were dried prior to compounding, in order to get a more homogeneous blend. In the following table 1, the type and amount of base polymer is specified, as well as the operational conditions of the compounder (temperature, mixing time and mixing rate).

TABLE 1

Samples mixed in compounder

| Sample | Base polymer | Base polymer amount (g) | PEO amount (g) | T (deg. C.) | Mixing time (mts) | Mixing rate (rpm) |
|---|---|---|---|---|---|---|
| A1 | T93 | 5 | 10 | 140 | 2 | 20 |
| A2 | T93 | 8 | 8 | 140 | 1.5 | 30 |
| A3 | PU | 5 | 10 | 140 | 2 | 30 |
| A4 | PU | 8 | 8 | 140 | 4 | 40 |
| A5 | T60 | 8 | 8 | 140 | 2 | 40 |
| A6 | PB | 10 | 5 | 170 | 4 | 50 |
| A7 | PB | 12 | 4 | 160 | 4 | 50 |
| A8 | PU | 10 | 5 | 140 | 1.5 | 50 |
| A9 | PU | 8 | 8 | 120 | 1.5 | 50 |

It was found that all the samples blended adequately, and in particular the polyurethane blended very well. This was also confirmed by study of films pressed out of the blended materials, and wetted for 30 seconds before being wiped off. By micrographs comparing the surface before and after wetting it was seen that structures were formed on the material, indicating migration out of the PEO.

Further, all the samples provided a much more slippery surface than the base polymer in itself when wetted.

In a further experiment, some of the samples, having PU or T93 as a base polymer, were placed in a vial filled with 1 mL water. After a certain time, ranging from 3 minutes to 1 hour, the water was analyzed, to determine the amount of PEO that had leached into the water. The analysis was made with fast liquid chromatography quadrupole time-of-flight mass spectrometry (LC-QTOF).

The results of this experiment are summarized in table 2 below, where the dimensions of the samples prior to wetting are specified, together with the weight of the sample, the leaching time (i.e. the time during which the sample was immersed in the water), the PEO content of the blend of the sample, the base polymer of the blend, and the determined PEO concentration of the water after leaching.

TABLE 2

Leaching of PEO into water

| Dimensions when non-wetted (mm) | Weight when non-wetted (g) | Leach time (mts) | PEO content in sample (wt %) | Base polymer | PEO concentration in the water (g/l) |
|---|---|---|---|---|---|
| 5 × 10 × 1.7 | 0.097 | 60 | 40 | T93 | 0.74 |
| 5 × 10 × 0.8 | 0.054 | 3 | 75 | PU | 0 |
| 6 × 10 × 1 | 0.061 | 3 | 50 | T93 | 0 |
| 5 × 10 × 1.5 | 0.11 | 3 | 75 | PU | 0 |
| 5 × 10 × 1.5 | 0.11 | 60 | 75 | PU | 2.51 |
| 5 × 10 × 1.5 | 0.09 | 30 | 75 | PU | 1.10 |
| 5 × 10 × 1 | 0.064 | 30 | 50 | T93 | 0.40 |
| 5 × 10 × 1.2 | 0.074 | 3 | 50 | PU | 0.10 |
| 5 × 10 × 1.2 | 0.077 | 30 | 50 | PU | 0.47 |
| 5 × 10 × 1.2 | 0.072 | 60 | 50 | PU | 1.05 |
| 5 × 10 × 1.2 | 0.061 | 60 | 50 | PU | 0.82 |
| 5 × 10 × 1 | 0.03 | 3 | 50 | PU | 0.04 |
| 5 × 10 × 1 | 0.049 | 30 | 50 | PU | 0.38 |

It can be seen that already within a few minutes, a substantial amount of PEO has leached out from many of the materials. This confirms the finding that PEO immediately begin to migrate from the surface when in contact with water. Further, it can be determined that the amount of leached out PEO increases with leaching time. Thus, the amount of migrated PEO can be controlled by inter alia control of the leaching time. Further, the amount of leached out PEO increases when the concentration of PEO in the blend is higher.

Thus, based on this, it is deduced that the migration of the hydrophilic polymer towards the surface of the substrate, and eventually into the surrounding fluid, can be very efficiently controlled inter alia by controlling how long the wetting is allowed to proceed prior to cross-linking. The leaching and migration effect only occurs prior to cross-linking, After cross-linking, it has been found that the migration immediately stops, and that essentially no hydrophilic polymer is leached out into the wetting liquid when the catheter is immersed.

In yet another line of experiments blends were prepared by a first run in a Brabender extruder, and then followed by a second run in the extruder, to blend the materials further, and to produce an extruded substrate. In the following table 3, the type and amount of base polymer is specified, as well as the operational conditions of the extruder temperature, mixing time and mixing rate).

TABLE 3

Samples mixed in extruder

| Sample | PU amount (wt %) | T93 amount (wt %) | PEO amount (wt %) | T (deg. C.) | Mixing time (mts) | Mixing rate (rpm) |
|---|---|---|---|---|---|---|
| B1 | 13 | | 87 | 120 | 2 | 70 |
| B2 | 33 | | 66 | 120 | 2 | 70 |
| B3 | 50 | | 50 | 120 | 2 | 70 |
| B4 | 66 | | 33 | 120 | 2 | 70 |
| B5 | | 25 | 75 | 120 | 2 | 70 |
| B6 | | 33 | 66 | 120 | 2 | 70 |

It was found that all the samples blended adequately, and in particular the polyurethane blended very well, and all the samples provided a much more slippery surface than the base material in itself when wetted.

Solid tubes were made by extrusion of these sample materials. Sample tubes were allowed to swell for 2 hours in water, and the swelling and wetting of the tubes were studied. When wetted, an outer layer of wetted, swelled material is formed around a core of non-wetted, un-swelled material. Over time, the outer layer increases in thickness, and the core diminishes gradually, to a point where the entire material is swelled. If the diameter of the solid tube initially is A, in un-swelled condition, and after 2 hours of swelling, the thickness of the swelled layer is b, and the diameter of the remaining inner core of un-swelled material is a, we consider the amount of swelling to be $(2 \times b)/(A-a)$ and the amount of wetting to be $(A-a)/A$. The swelling and wetting of the samples is presented in the table below.

TABLE 4

Swelling and wetting

| Sample | Swelling (%) | Wetting (%) |
|---|---|---|
| B1 | 158 | 100 |
| B2 | 144 | 76 |
| B3 | 147 | 63 |
| B4 | 129 | 60 |
| B5 | 243 | 82 |
| B6 | N/A (boundaries became to diffuse to enable measuring) | 63 |

It can be deduced from this that blends with PU swells less than blends with T93 as base polymer, but the percentage of the tube that has been wetted after 2 hours is comparable. In general, for both types of base polymers, a higher ratio of PEO provides a faster wetting process and a higher degree of swelling.

The tubes were then packaged in gas impermeable packages together with different amounts of water, but in a volume that assured complete wetting of the tubes. Tubes packaged with less water were hence packaged in smaller container, with a "tighter" fit. The assemblies were further subject to irradiation at 56 kGy after one hour.

Further, the friction and durability of the hydrophilic surface layer of the tubes were in all cases subjectively determined to be very good. However, in order to confirm this, some of the samples were evaluated using a Harland FTS Friction Tester, available from Harland Medical Systems, with a clamp force of 100 g and a pull speed of 1.0 cm/s. For some of the samples, the friction measurement was also done repeatedly for several times, in order to determine the durability of the hydrophilic surface layer. The results of this are presented in the table below.

TABLE 5

Friction coefficient

| Sample | Friction (1$^{st}$ time) | Friction (5$^{th}$ time) | Friction (10$^{th}$ time) |
|---|---|---|---|
| B3 | 0.083 | 0.133 | 0.166 |
| B4 | 0.093 | N/A | N/A |
| B5 | 0.098 | 0.096 | 0.100 |
| B3 - tight | 0.091 | 0.090 | 0.091 |

Thus, all samples showed a very low friction coefficient, which is in all cases similar to the friction coefficient of the best commercially available hydrophilic urinary catheters on the market today, such as the hydrophilic urinary catheters sold as LoFric® by Wellspect HealthCare (previously Astra Tech).

Further, the hydrophilic surface layer is in all cases very durable, with limited deterioration when subject to the extensive wear of 5 or 10 measurement cycles. In two of the samples, the hydrophilic surface layer appears to be totally unaffected by this wear.

"B3—tight" was a sample packed with a very limited amount of water. Since the PEO leached out from the catheter cannot diffuse away from the surface, it formed a more compact gel around the material. This improved the durability of the hydrophilic surface layer.

Further, some packed and cured B3 samples were aged in a climate chamber for 6 months. No signs of degradation of the material could be detected.

Further, the B4 blend was used to extrude catheter tubes, and after cutting one end was formed into a catheter tip through melting and molding, and holes were punched out using a side punch. The produced catheter was found to be useable as a urinary catheter, and have comparable properties and characteristics as urinary catheters on the market today. Further, the friction coefficients of the catheter was found to be the same as for the solid tubes discussed above.

In a further experiments, PEO was blended with PE in a compounder. Various compositions of the blend was used, some with a compatibilizer (Fusabond E226 from DuPond). Small amounts of filler was also added in some of the samples. The compositions of the samples are presented in Table 6 below.

TABLE 6

Samples mixed in compounder

| Sample | Base polymer PE (wt %) | PEO amount (wt %) | Compatibilizer amount (wt %) | Calcium carbonate amount (wt %) | T (deg. C.) | Mixing time (mts) | Mixing rate (rpm) |
|---|---|---|---|---|---|---|---|
| C1 | 84 | 10 | 6 |   | 190 | 2 | 20 |
| C2 | 78 | 10 | 6 | 6 | 190 | 2 | 20 |
| C3 | 40 | 48 | 12 |   | 180 | 2 | 20 |

All the compounds blended very well. This was also confirmed by study of films pressed out of the blended materials, and wetted for 60 seconds before being wiped off. By micrographs comparing the surface before and after wetting it was seen that structures were formed on the material, indicating migration out of the PEO.

Further, all the samples provided a much more slippery surface than the base material in itself when wetted.

In yet further experiments, PEO was blended with PU, and PVP with PU, respectively, in a compounder. The compositions of the samples are presented in Table 7 below.

TABLE 7

Samples mixed in compounder

| Sample | Base polymer PU amount (wt %) | PEO amount (wt %) | PVP amount (wt %) | Calcium carbonate amount (wt %) | T (deg. C.) | Mixing time (mts) | Mixing rate (rpm) |
|---|---|---|---|---|---|---|---|
| D1 | 60 | 20 |   | 20 | 140 | 1 | 30 |
| D2 | 80 |   | 20 |   | 150 | 5 | 50 |
| D3 | 60 | 20 | 20 |   | 150 | 5 | 50 |

Again, all the compounds blended adequately well. This was also confirmed by study of films pressed out of the blended materials, and wetted for 60 seconds before being wiped off. By micrographs comparing the surface before and after wetting it was seen that structures were formed on the material, indicating migration out of the PEO and PVP, respectively.

Again, all the samples provided a much more slippery surface than the base material in itself when wetted.

CONCLUSION AND SUMMARY

The invention has now been discussed in relation to different embodiments. However, it should be appreciated by those versed in the art that several further alternatives are possible. For example, the features of the different embodiments discussed above may naturally be combined in many other ways.

It is further possible to use the invention for other types of medical devices, and for example for other types of catheters than urinary catheters, such as vascular catheters or the like.

Many different materials could also be used for the different parts of the catheter assembly. Specifically, other blends of various base polymers and hydrophilic polymers may be used, and additives, such as fillers, compatibilizers etc may be included. It is also possible to include e.g. an osmolality increasing agent, such as NaCl directly in the polymer blend.

It will be appreciated by those versed in the art that several such alternatives similar to those described above could be used without departing from the spirit of the invention, and all such modifications should be regarded as a part of the present invention, as defined in the appended claims.

The invention claimed is:

1. A medical device comprising a substrate, having on its surface, on at least a part thereof, a hydrophilic surface layer providing low-friction surface character of the medical device when wetted by a wetting fluid, wherein at least one base layer is arranged as an extruded layer on the substrate, said base layer including said hydrophilic surface layer, is made of a polymer blend comprising at least one predominantly hydrophobic base polymer and at least one outer hydrophilic polymer, the base layer comprising said outer hydrophilic surface layer, an interior base layer and a transition layer, arranged between the interior base layer and the hydrophilic surface layer, wherein the concentration of said at least one hydrophilic polymer is higher in the hydrophilic surface layer than in the rest of the base layer, wherein the polymers in said hydrophilic surface layer are crosslinked, and wherein the transition layer provides a gradual increase in concentration of the at least one hydrophilic polymer from the interior base layer towards the hydrophilic surface layer, wherein, when in a dry state, the interior base layer comprises 25-75 wt % of the at least one hydrophilic polymer and the hydrophilic surface layer comprises at least 80 wt % of the at least one hydrophilic polymer.

2. The medical device of claim 1, wherein the at least one hydrophilic polymer comprises at least one material selected from: polyvinyl compounds, polysaccharides, polyurethanes, polyacrylates or copolymers of vinyl compounds and acrylates or anhydrides, poly (alkyl ether), i.e. polyethylene oxide or polypropylene oxide, polyoxyethylene, polyethylene oxide, polyvinyl-pyrrolidone, heparin, dextran, xanthan gum, polyvinyl alcohol, hydroxy propyl cellulose, methyl cellulose, copolymer of vinylpyrrolidone and hydroxy ethylmethyl acrylate or copolymer of polymethylvinyl ether and maleinic acid anyhydride, and copolymers thereof.

3. The medical device of claim 1, wherein the at least one hydrophilic polymer comprises at least one of polyethyleneoxide, poly(acrylic acid), polyvinyl-pyrrolidone and polysaccharide.

4. The medical device of claim 1, wherein the at least one hydrophilic polymer has a molecular weight of at least 50 kDa.

5. The medical device of claim 1, wherein the at least one base polymer comprises at least one of polyolefin and polyurethane.

6. The medical device of claim 1, wherein the medical device is a catheter.

7. The medical device of claim 1, wherein the substrate further comprises a filler material.

8. The medical device of claim 7, wherein the filler material comprises a calcium carbonate filler.

9. The medical device of claim 1, wherein the interior base layer comprises at least two different sub-layers, wherein an outer sub-layer, being closer to the hydrophilic surface layer, has a higher concentration of the at least one hydrophilic polymer than an inner sub-layer, being farther from said hydrophilic surface layer.

10. The medical device of claim 9, wherein said at least two different sub-layers are coextruded together.

11. A medical device assembly, comprising a medical device of claim 1, a container and a wetting fluid, wherein said container houses at least a part of the medical device together with the wetting fluid, so that the hydrophilic surface layer is maintained in a wetted state.

12. The medical device of claim 1, wherein the material composition of the hydrophilic surface layer when in a dry state comprises at least 95 wt % of the at least one hydrophilic polymer.

13. The medical device of claim 1, wherein the polymer blend in the interior base layer comprises 25-50 wt % of the at least one hydrophilic polymer.

14. The medical device of claim 1, wherein the polymer blend in the interior base layer comprises 50-75 wt % of the at least one base polymer.

15. The medical device of claim 1, wherein the at least one hydrophilic polymer has a molecular weight of at least 200 kDa.

16. The medical device of claim 1, wherein the medical device is a urinary catheter, wherein the hydrophilic surface layer is provided at least on an insertable part thereof.

17. The medical device of claim 1, wherein the concentration of the at least one hydrophilic polymer is essentially the same in the entire interior base layer.

18. The medical device of claim 1, wherein the interior base layer forms at least 95% of the total thickness of the base layer.

19. The medical device of claim 1, wherein the at least one base polymer comprises at least 75 wt % of polyolefin and/or polyurethane.

* * * * *